United States Patent [19]

Koester

[11] 4,241,257
[45] Dec. 23, 1980

[54] SCANNING MICROSCOPIC APPARATUS

[76] Inventor: Charles J. Koester, 4940 Pine Ledge West, Clarence, N.Y. 14031

[21] Appl. No.: 42,085

[22] Filed: May 24, 1979

Related U.S. Application Data

[62] Division of Ser. No. 902,277, May 3, 1978, Pat. No. 4,150,264.

[51] Int. Cl.³ ............................................ H01J 3/14
[52] U.S. Cl. .................................. 250/235; 350/6.7
[58] Field of Search ............... 350/6.5, 6.6, 6.7, 6.8, 350/6.9, 6.91; 250/216, 234, 235, 236, 563, 202, 203; 358/206, 207, 208, 285, 293

[56] References Cited

U.S. PATENT DOCUMENTS

| | | | |
|---|---|---|---|
| 3,602,572 | 8/1971 | Norris | 350/6.7 |
| 3,705,755 | 12/1972 | Baer | 250/236 |
| 3,775,735 | 11/1973 | Funk et al. | 358/293 |
| 4,019,811 | 4/1975 | Lorah et al. | 350/6.5 |

Primary Examiner—David C. Nelms
Attorney, Agent, or Firm—Sandler & Greenblum

[57] ABSTRACT

A scanning optical system for incrementally generating a composite image of a strip-scanned object. A light beam is swept by a first rotating mirror across the object to scan-illuminate same. Imaging light from the object is then projected to an intermediate image station across which it is swept by a second rotating mirror. A stationary aperture at the intermediate image station transmits or reflects, at any instant, only a desired incremental image of the scanned object. This desired incremental image is in turn relayed to a final image plane by reflection from a third rotating mirror so as to synchronously lay down on the image plane a composite of the instantaneous increments.

40 Claims, 21 Drawing Figures

SCANNING MICROSCOPIC APPARATUS

This is a division of application Ser. No. 902,277 filed May 3, 1978, now U.S. Pat. No. 4,150,264.

BACKGROUND OF THE INVENTION

This invention relates generally to apparatus and method for microscopic examination of a predetermined object field or plane within biological tissue.

In examining microscopic specimens of some thickness, the desired image is often obscured by light scattered from within the volume of the sample itself. This is particularly true of specimens examined by incident or reflected light, that is, when the illumination and viewing are from the same side of the specimen.

The light scattering within the volume of the specimen above and below the plane of interest is reduced if only a small region is illuminated. The scattered light is further reduced if the illuminating light directed onto the object field follows a different path through the scattering medium than does the imaging light propagating from the object field.

A specific problem is the examination of the emdothelial cell layer on the inner surface of the cornea of the human eye. These cells are responsible for maintaining the proper water content of the cornea, to prevent swelling and opacification of the cornea. To examine these cells it has been found effective to illuminate a narrow strip of cells using half the aperture of a microscope objective, and to use the other half of the aperture for viewing the cell layer.

The problem addressed by the present invention is the relatively small area which can be viewed or photographed by this method. The strip is typically only about 100 $\mu$m wide and perhaps 400 $\mu$m long. Even within this narrow strip the image quality is not uniform, generally being partially obscured by scattered light on one side. If a larger area is to be studied, it must be photographed sequentially in strips, which are then placed together as a composite.

Previous solutions to this problem have included a synchronized translation of the tissue and of the recording film. This solution is suitable for study of excised tissue but is not satisfactory for the living eye. Another solution suitable for in vitro studies employs two dimensional scanning of a microscope objective. A third suggested solution has employed a rotating Nipkow disc. While these solutions have shown some success for in vitro studies of excised tissue, they have not been successful in studies on living human eyes. The principal reason is the fact that the living human eye is in nearly constant motion, with only short intervals of time between small rotational movements, called saccades. Therefore, any scanning of such a subject must be done in an elapsed time which is short compared to the time between saccades.

Further solutions to the small field problem were proposed by U.S. Pat. No. 3,547,512 to Baer. The Baer arrangement employs an assembly of two slits and a mirror which oscillate as a unit about a specific axis of rotation. The motion of each slit must be equal to or greater than the width of the image which is produced. Uniform illumination must be provided over an area equal to the area of the image which is produced. Another solution employs one or more pairs of appropriately spaced slits located on a disc which rotates in its plane. This also requires a fairly large moving element and uniform illumination over an area the size of the final image.

SUMMARY OF THE INVENTION

It is an object of this invention to provide apparatus and methods for illuminating and viewing a strip within a specimen and scanning the strip in a direction transverse to its long dimension so that a two dimensional image is produced. The illuminating and imaging light beams pass through different portions of the aperture of the microscope objective or other imaging lens, so as to minimize the scattered light from out-of-focus portions of the specimen. The moving part is a mirror of one, two or three plane faces, which may be of small dimension. Since the moving part is small, it can more readily be scanned rapidly, so that an image is produced in a time short compared to the time between eye saccades. For example, a mirror in the form of a 1 cm cube in one version of this instrument, is oscillated at 500 Hertz, so that a flash lamp of 1/1000 sec. duration, properly synchronized, illuminates a full scan of the mirror in one direction.

A further object is to permit an improved image by allowing the slit to be narrower than is presently used in so called specular or endothelial microscopes. In the invention the slit width can be selected for the best image quality, providing only that adequate light is available to produce the image or photographic exposure.

It is also an object to provide an instrument which can be used to view and photograph the endothelial cell layer either in vivo or in vitro.

Finally, a general object is to provide an instrument which will permit examination of a predetermined plane, within a scattering or transparent medium, of an object which is illuminated and viewed from the same side.

The present invention is effective to scan a strip of illumination across the desired object plane, to synchronously scan a slit-shaped viewing aperture across the same object plane, and finally to reconstruct an image thereof by scanning the image of the slit-shaped viewing aperture across a film plane or eyepiece image plane. The scanning is accomplished by three reflections from mirror surfaces which are rotating or oscillating in a rotary motion. To say it another way, the invention makes use of three reflections from a rotating mirror. The mirror may consist of one, two, or three plane faces. Alternatively, two or three synchronously rotating mirrors may be used. An illuminated stationary slit is imaged on the desired plane in the specimen. The slit image is scanned by the first reflection from the rotating mirror to illuminate the specimen. Image light reflecting and returning from the specimen is reflected a second time by the rotating mirror and imaged on a second slit, which is also stationary. This second slit serves to select only that portion of the object or specimen plane which is illuminated by the first slit and to eliminate or mask out all extraneous light, as from light scattering centers elsewhere in the specimen. Continuing, image light propagating from the second slit is reflected a third time from the rotating mirror and brought to a focus at the image plane. The effect of the third reflection is to scan the slit image across the image plane in synchronism with the scan of the illuminated slit in the specimen.

In the description which follows the word rotating is intended to mean either continuously rotating or rotating in an oscillatory manner. In addition, the eye is shown as the specimen to be examined by this system. This is only exemplary of an environment and use of this invention. It should be kept in mind that the system is equally useful in examining other biological specimens and sundry other objects in which the desired detail may be obscured by scattered light from within the volume of the specimen.

DETAILED DESCRIPTION OF THE ILLUSTRATED EMBODIMENT

Figure 1:
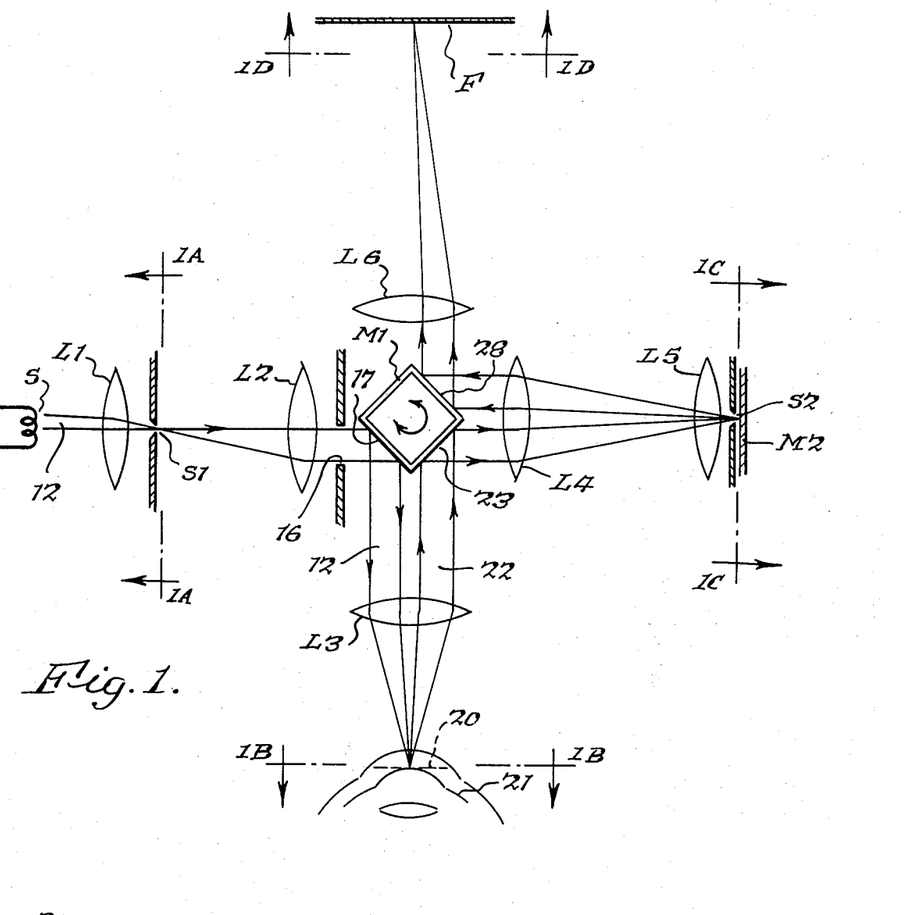
FIG. 1 is a simplified plan diagram of the presently preferred exemplary embodiment of this invention, utilizing a three facet rotating mirror.
Figure 1A:
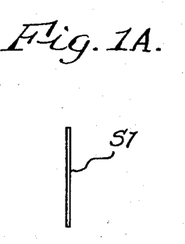
FIGS. 1A, 1B, 1C and 1D are schematic of views taken respectively in directions 1A, 1B, 1C and 1D in FIG. 1.
Figure 1B:
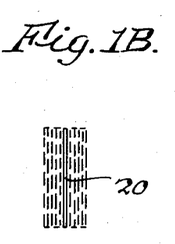
Figure 1C:
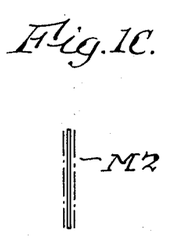
Figure 1D:
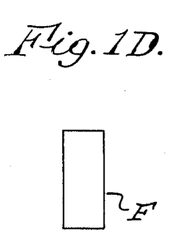

Referring first to FIG. 1, a light source S generates an illumination light bundle 12 which is collected by a condenser lens L1 and passes through a slit S1. Slit S1 is preferably of variable width. A collimating lens L2 collimates the light from flit S1, and directs it through an aperture 16 to a reflecting facet 17 of a rotatable mirror M1. After reflection from facet 17 the light bundle 12 is incident on an objective lens 13, a microscope objective, which focusses the image of slit S1 on a desired object plane 20 within the volume of a specimen or object 21. It is to be noted that illumination light is directed at the object plane 20 through only about half of the aperture of lens L3.

Light which is reflected or scattered at the desired object plane in the specimen is shown as an image light ray bundle 22, which is collimated by the objective lens L3 and directed to a reflecting facet 23 of mirror M1. After reflection from facet 23, the image light bundle 22 is focussed by a relay lens L4 at a stationary slit S2. The imaging light bundle 22 which has been chosen for illustration is that which propagates from the illuminated portion of the desired object plane 20, within the specimen 21, to the stationary slit S2 via the optics consisting of objective lens L3, reflector facet 23 and relay lens L4. Other light from the illuminated portion of plane 20 may be scattered in other directions, and will not be collected and imaged by the optics and will therefore not contribute to the image. And light rays scattered from other portions of the specimen will not in general pass through slit S2. Slit S2 is preferably of variable width, so as to match the width of the image of slit S1.

Since the object plane 20 is imaged onto the plane of slit S2 the two planes are said to be conjugate. Thus the slit S2 is conjugate to a slit shaped region of plane 20. The microscope is adjusted so that this slit shaped region is coincident with the image of slit S1 at the desired object plane 20 in the specimen. Both slit images are scanned across the selected plane 20 in the specimen as the mirror M1 rotates.

The function of slit S2 is to pass only image light from the narrow strip in the specimen illuminated by the image of slit S1. The jaws of the slit S2 are blackened so that light from other regions of the specimen which strikes the jaws and not the slit S2 will not be reflected back into the system. Mirror M2, adjacent to the stationary slit S2, reflects the light which has passed through slit S2 back through the slit S2, through lenses L5 and L4 to the third reflector facet 28 of rotating mirror M1. A projection lens L6 projects an image of slit S2 on the image plane F at which a recording film is preferably disposed. Because of the reflection from the rotating mirror this final image of the slit S2 is scanned across the film.

Lens L5 is a field lens, the function of which is to image the aperture which precedes the lens onto the aperture which follows the lens. In this case, the field lens L5 is effective to image facet 23 of rotating mirror M1 onto facet 28. This assures that light from the entire illuminated length of the slit S2 will be transmitted to the final image plane.

It is understood that for visual observation an eyepiece may be used to view the image plane F, in addition to or instead of a recording film. Or, for electro-optic display, an image sensor coiuld be substituted for the film. The term "image sensor" is used to signify any of the several types of television camera tubes or solid state detector arrays used for the purpose of converting an optical image to an electrical signal.

In this diagram it has been assumed that objective lens L3 is a microscope objective which is infinity corrected. That is, the optics have been designed so that aberrations are minimized when light from a point in the object plane emerges from the objective as a bundle of parallel rays. Such infinity corrected objectives are sold by several manufacturers. If a non-infinity corrected objective is used, the system can easily be adapted by techniques known to those skilled in the art. For example, a negative lens of proper focal length can be inserted in the space between rotating mirror M1 and the objective lens L3. Or a system with fewer lenses can be constructed by placing slits S1 and S2 at the proper tube length from objective lens L3, thus eliminating the need for lenses L2 and L4.

While for illustrative purposes a filament has been shown as the light source in FIG. 1, it is necessary to use a flash lamp for photography of the living eye to eliminate any blurring due to motion of the eye during exposure. The flashlamp should be located at the position of the source (filament) in FIG. 1. In many cases, it is convenient to utilize both a continuous source such as a filament and a flash source. One commonly used method is to image the continuous source onto the flashlamp in such a way that light from the source will pass through the transparent flashlamp and then into the rest of the optical system.

Figure 2:
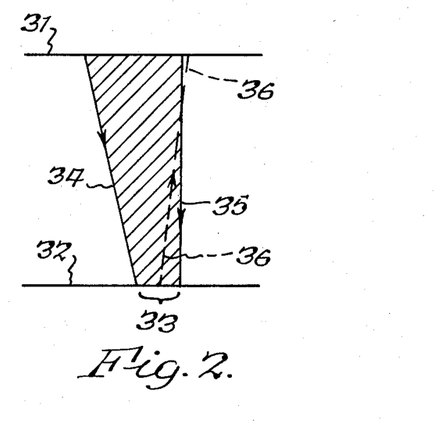
FIG. 2 is a schematic illustration of the illuminating and imaging light from a relatively large slit width.
Figure 3:
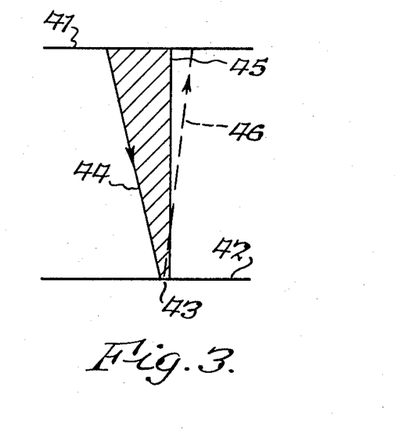
FIG. 3 is an illustration, similar to FIG. 2, of illuminating and imaging light from a relatively narrow slit.

FIGS. 2 and 3 illustrate schematically how unwanted stray light can be generated by scattering within the volume of the specimen, such as a cornea, and how the use of a narrow slit minimizes the problem. In FIG. 2 a 100 micrometer slit image width is assumed, and an illumination bundle of $NA = 0.33$. In the cornea, a ray with $NA = 0.33$ will be at an angle A with respect to the axis, where $\sin A = 0.33/n$ and n, the index of refraction of the cornea equals 1.37. 31 is the first surface of the cornea, 32, the second. 33 is the 100 micrometer wide image of slit S1 on the second surface of the cornea 32. Slit image 33 is also the part of object plane 20 under observation (being imaged) at any instant. For aid in understanding 33 may also be thought of as object strip 33. Rays 34 and 35 represent the outer limits of the illuminating bundle, ray 34 being the NA 0.33 ray illuminating the left edge of the slit image, and ray 35 being the NA 0.0 ray illuminating the right edge of the slit image. The shaded area between rays 34 and 35 represents the volume of the cornea or specimen which is illuminated and which can scatter light back into the objective lens. Imaging ray 36 represents the principal image forming ray from the center of the slit image or object strip 33. For purposes of illustration ray 33 has been shown at an angle of 7° to the axis, which corresponds to a ray in the middle of the NA 0.33 bundle in the cornea, i.e. at NA 0.165. It is to be noted that this ray travels almost the entire thickness of the cornea in the illuminated volume. At any point along this ray in this illuminated volume, light scattered in the same general direction as the imaging ray 36 can contribute to stray light in the image. In otherwords, any point in the illuminated volume which also lies within the image light bundle can become a source of unwanted light scatter in the image bundle.

For comparison, FIG. 3 shows at 43 a 20 micrometer wide image of slit S1. Rays 44 and 45 are the outer limits of the illuminating bundle in this case. Imaging ray 46 is the same as imaging ray 36 in FIG. 2. It is to be noted that the path of imaging ray 46 is through only a small portion of the illuminated volume. Therefore the scattered light from the illuminated volume using a 20 micrometer slit width will be much reduced compared to that from the 100 micrometer wide slit.

FIG. 2 also illustrates one reason for unequal image quality over the width of a 100 micrometer wide slit. Image forming light from the left part of image 33 must pass through an illuminated volume of the cornea which is relatively thick. Therefore the corresponding portion of the image will exhibit a large amount of veiling glare light. On the other hand, image forming light from the right portion of slit image 33 travels through a relatively thin illuminated volume. The corresponding portion of the image will be relatively free of stray light. Thus one side of the slit image will exhibit more veiling glare superimposed on the image detail than will the other side.

Scanning provides two benefits. First, this non-uniformity of image quality is removed by the scanning. Second, scanning permits the use of a narrow slit, which gives an image with less scattered light than does the wide slit.

Figure 4:
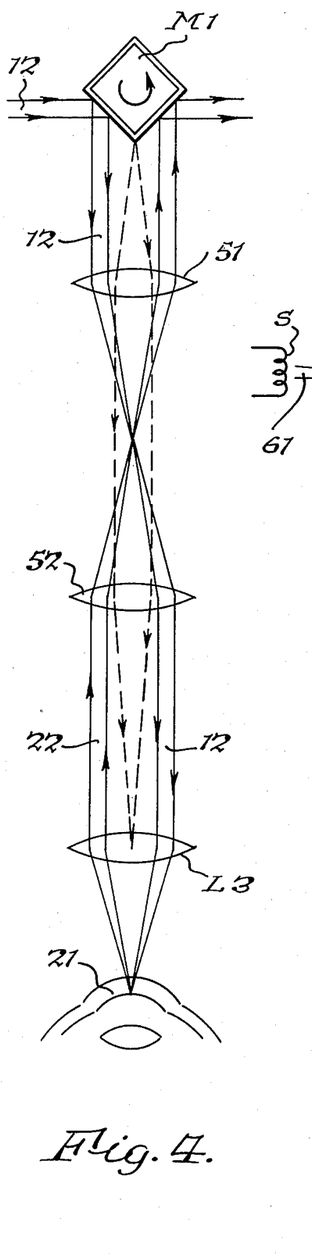
FIG. 4 is a simplified plan view of a relay system which may be used in conjunction with the embodiment shown in FIG. 1.

In FIG. 4 a relay system is shown, the purpose of which is to accomplish the precise control over the illumination ray bundle as described in connection with FIGS. 2 and 3. If the rotating mirror M1 is located some distance from objective lens L3 as shown in FIG. 1, the rays will pass through different portions of objective lens L3 as the mirror rotates. In FIG. 4 lenses 51 and 52 act together as a unit power afocal telescope which images the apex of mirror M1 on the lens L3 as represented by the phantom lines. Then as mirror M1 rotates the reflected rays will always pass through the same portion of lens L3. To be precisely accurate the preceding statement must be modified in two respects. First, the mirror would have to rotate about its apex rather than its center. Second, if lens L3 is a thick lens, as will be the case for a microscope objective, the mirror apex should be imaged on the second principal plane of lens L3. The second condition can be accomplished by proper focussing of the mirror and lens L3 relative to the afocal telescope. The first condition may be accomplished by design of the mirror rotating mechanism. But in the case of a small mirror and small angular rotation the mirror may rotate about the center of gravity for example with little deliterious effect.

The fact that lenses 51 and 52 constitute an afocal telescope means that parallel rays 12 from mirror M1 are again parallel as they impinge on objective lens L3. Similarly parallel rays 22 emerging from lens L3 will again be parallel as they are incident on mirror M1.

Figure 5:
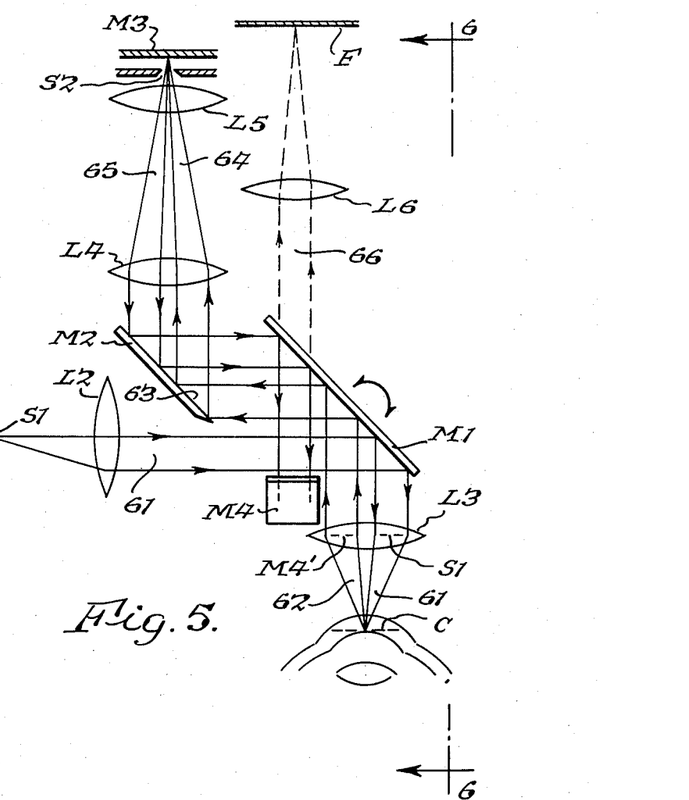
FIG. 5 is a simplified plan diagram of a second exemplary embodiment of this invention, utilizing a single plane rotating mirror.

FIG. 5 illustrates the use of a single rotating plane mirror M1 to perform the simultaneous illumination and image scanning. Light 61 from source S is collected by condenser lens L1 and passes through slit S1. Collimating lens L2 reimages source S on a portion of objective lens L3. Slit S1 is imaged by the combined action of lenses L2 and L3 onto the desired plane, C. Light 62 returning from this plane is collimated by the objective lens L3 and is then incident on a portion of mirror M1 adjacent to the portion thereof reflecting the illuminating beam 61.

After reflection from mirror M1 the light is incident on mirror M2 at position 63. Relay lens L4 then brings the light to focus at stationary slit S2, which serves the same function as slit S2 in FIG. 1.

After the light passes through slit S2 it is reflected by mirror M3, again passes slit S2 and field lens L5. Field lens L5 serves the same function as field lens L5 in FIG. 1, except that in this case lenses L5 and L4 together image the left portion of objective lens L3 on mirror M4. Since mirror M4 is then conjugate to objective lens L3, it defines the portion of the lens L3 through which the image forming rays pass. Alternatively M4 may be a larger mirror with an adjacent aperture stop.

It is to be noted that in this arrangement the illumination and image forming rays are constrained to pass through different portions of lens L3; this function is accomplished by imaging the source S and the mirror M4 on different portions of lens L3, at S' and M4' respectively. It may be necessary in some instances to employ a relay system such as shown in FIG. 4 to keep the bundles passing through the same portion of the lens L3 for all positions of the mirror.

Figure 6:
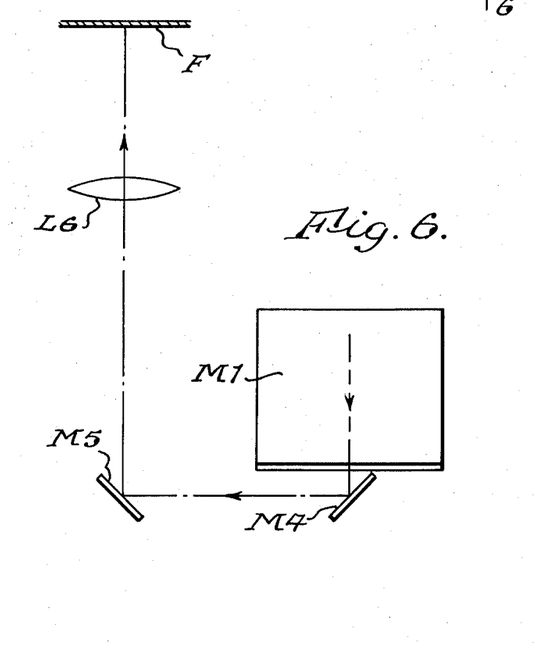
FIG. 6 is an elevation diagram of a portion of the apparatus in FIG. 5.

FIG. 6 is an elevation diagram of a portion of FIG. 5. illustrating the path of the light from mirror M1 to mirrors M4 and M5, through lens L6 and to the film F. Thus rays 66 pass above mirror M1. This is illustrated schematically in FIG. 5 by showing the rays as dashed lines.

Alternatively, mirror M4 could reflect the light directly to a camera directed perpendicular to the plane of the paper or mirror M4 could reflect the light directly to a viewing system.

Other arrangements are possible in which a single plane mirror can be used to accomplish the desired functions: namely scanning of an image of the illuminated slit, stabilization of the scanned slit image, isolation by means of a slit, and final scanning to reconstruct the composite image. The common factor is to have three reflections from a rotating mirror. To minimize problems with stray light it is preferable to use separate areas of the mirror for each reflection.

Figure 7:
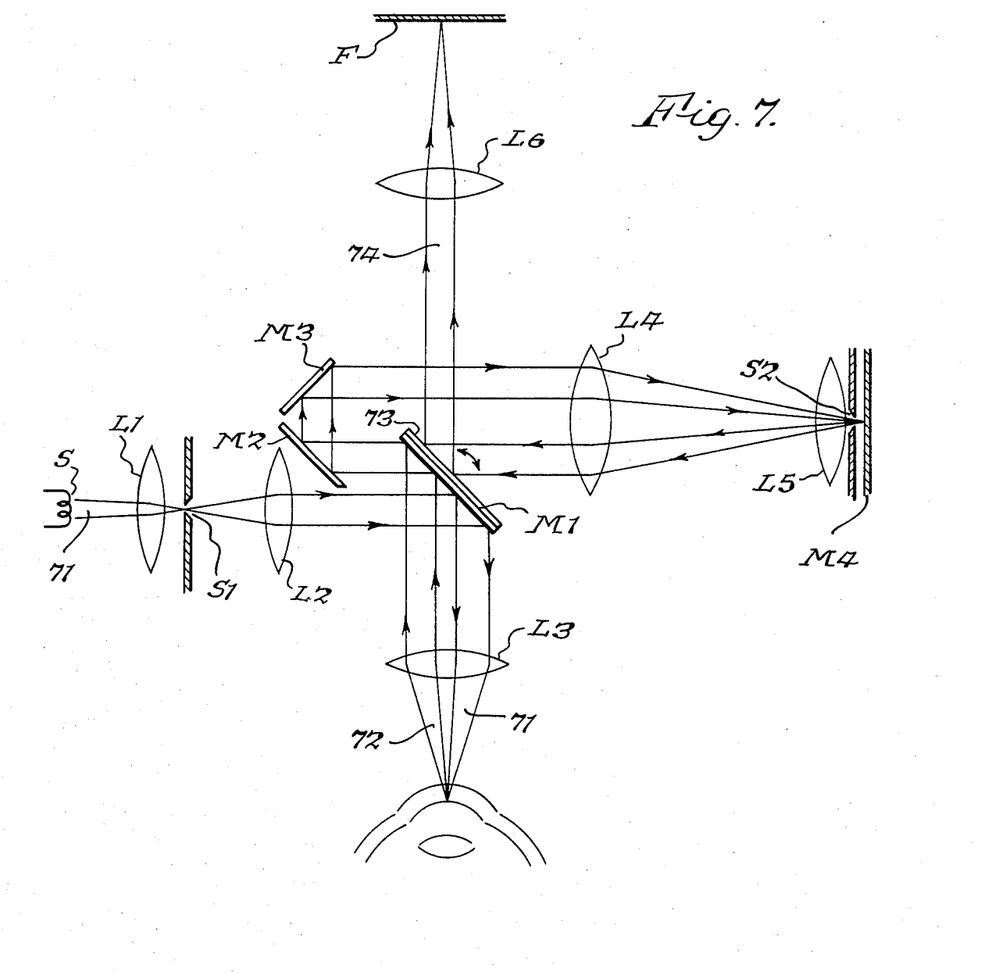
FIG. 7 is a simplified plan diagram of a third exemplary embodiment of this invention, utilizing a rotating mirror with two reflecting facets.

FIG. 7 illustrates a scheme in which a mirror with two facets is utilized to accomplish the desired functions. Again there are three reflections, two from the first facet and one from the second facet. Light 71 from the source S is collected by condenser lens L1, passes through slit S1. Collimating lens L2 collimates light from the slit S1, directing it to a portion of rotating mirror M1. After reflection the light is focused by objective lens L3 to an image of slit S1 in the specimen. The rotary motion of mirror M1 causes the slit image to scan across the desired plane in the specimen. Light 72, reflected or scattered by detail in the specimen, is collimated by lens L3 and directed to a portion of mirror M1 adjacent to the portion used for the incident light 71. After reflection from mirror M1, the light is incident on mirrors M2 and M3 which direct the light to lens L4, located on the reverse side of mirror M1. Lens L4 focuses the slit image onto slit S2, which serves the same function as slit S2 in FIG. 1. Mirror M4 reflects the light back through slit S2 and thence to the lens L4 and to the second facet 73 of mirror M1. Field lens L5 serves to image mirror M3 onto Mirror M1 after reflection of the light at mirror M4.

After reflection from the second facet 73 of mirror M1 the image forming bundle 74 is focused by lens L6 to the film plane F. Alternatively an eyepiece or TV camera tube could be substituted at the film plane.

The light source in FIGS. 1, 5 and 7 is shown in simplified form. In many cases it is desirable to add a condenser and an aperture stop, to provide a better controlled light source.

Figure 8:
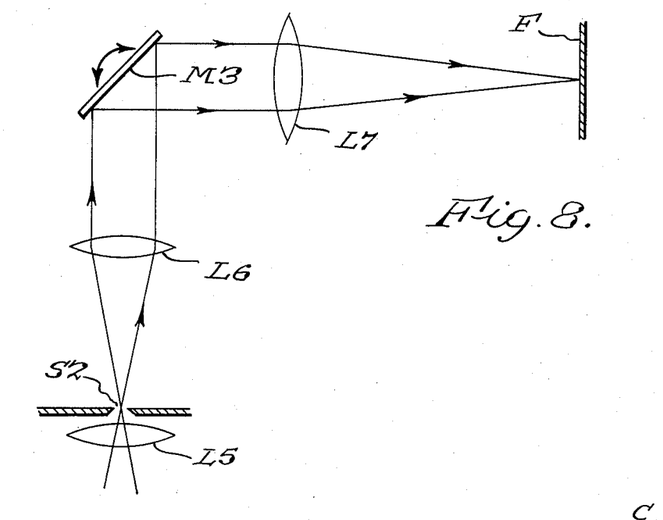
FIG. 8 is a plan diagram of an optional image reconstruction system, which can be utilized in connection with a portion of the apparatus shown in FIGS. 1, 5 or 7.

To those skilled in the art it will be apparent that the second and third reflections need not be from the same mirror as the first reflection, but may be from synchronously rotating mirror or mirrors. FIG. 8 illustrates an alternative to a portion of FIG. 5. Consider FIG. 8 as positioned atop FIG. 5. Lens L5 and slit S2 are the same as in FIG. 5 but mirror M3 of FIG. 5 has been removed. In FIG. 8 after passing through the slit S2 the light passes to lens L6, reflects from the rotating mirror M3, and is focussed by lens L7 on the film F. Mirror M3 must rotate synchronously with mirror M1. This can be accomplished by a number of techniques. One method is to use essentially identical oscillating mirrors M1 and M3, and to drive them from the same source of AC power. Experience indicates that certain such mirrors are more easily synchronized if they are driven at a frequency which is substantially different from their resonant frequency. Care must be taken to assure that the sense of rotation of mirror M3 is correct, so that the image on the film is properly reconstructed. For example, if FIG. 8 is combined with FIG. 5, when mirror M1 is rotating clockwise mirror M3 must also be rotating clockwise.

There are two distinct advantages to this system involving two rotating mirrors. First the crowding of optical elements and optical paths around mirror M1 is eased. Second, the slit S2 will be absolutely opaque to all light except that which passes between the jaws. In FIG. 5, the jaws of the slit must be blackened to prevent unwanted light from being reflected back toward lens L4. While blackening can be reasonably effective, it is not possible to achieve total blackness or zero reflection. And methods which approach 100% efficiency are often more involved than a simple slit mechanism.

The camera can be removed still farther from the rotating mirror, etc., by employing a fiber optics bundle. The bundle could consist of a single row of fibers, with the receiving end of the row placed immediately behind the slit S2 in FIGS. 1, 5, 7 or 8. The other end (the emitting end) of the row of fibers is positioned at the first focal plane of lens L6 in FIG. 8, so that the image is reconstructed by the scanning of mirror M3.

A preferred arrangement would be to employ a bundle of fibers consisting of several rows of fibers and a slit wide enough to expose several rows. The placement of the ends is exactly the same as for the single row discussed above. The advantages are that the image will have a more even illumination, and the resolution will be improved over that obtained with a single row of fibers, other conditions being equal.

It will be apparent to those skilled in the art that other arrangements may be used to accomplish the same purpose as that illustrated in FIG. 8. For example, instead of using a rotating mirror to produce the scanning action, it is possible to focus the slit S2 directly on an image plane by means of an image relay system consisting of one or more lenses and to move this image relay system in synchronism with the illumination scan. The image plane referred to above may be the final image plane or an intermediate relay image plane. Second, the recording medium (e.g. film) can be located immediately behind the slit and can be moved synchronously with the illumination scan. A third arrangement is to utilize a flexible image transmitting bundle of optical fibers, the entrance end of the bundle located directly behind slit S2, and the exit end of the bundle arranged to scan across an image plane in synchronism with the illumination scan.

Figure 9:
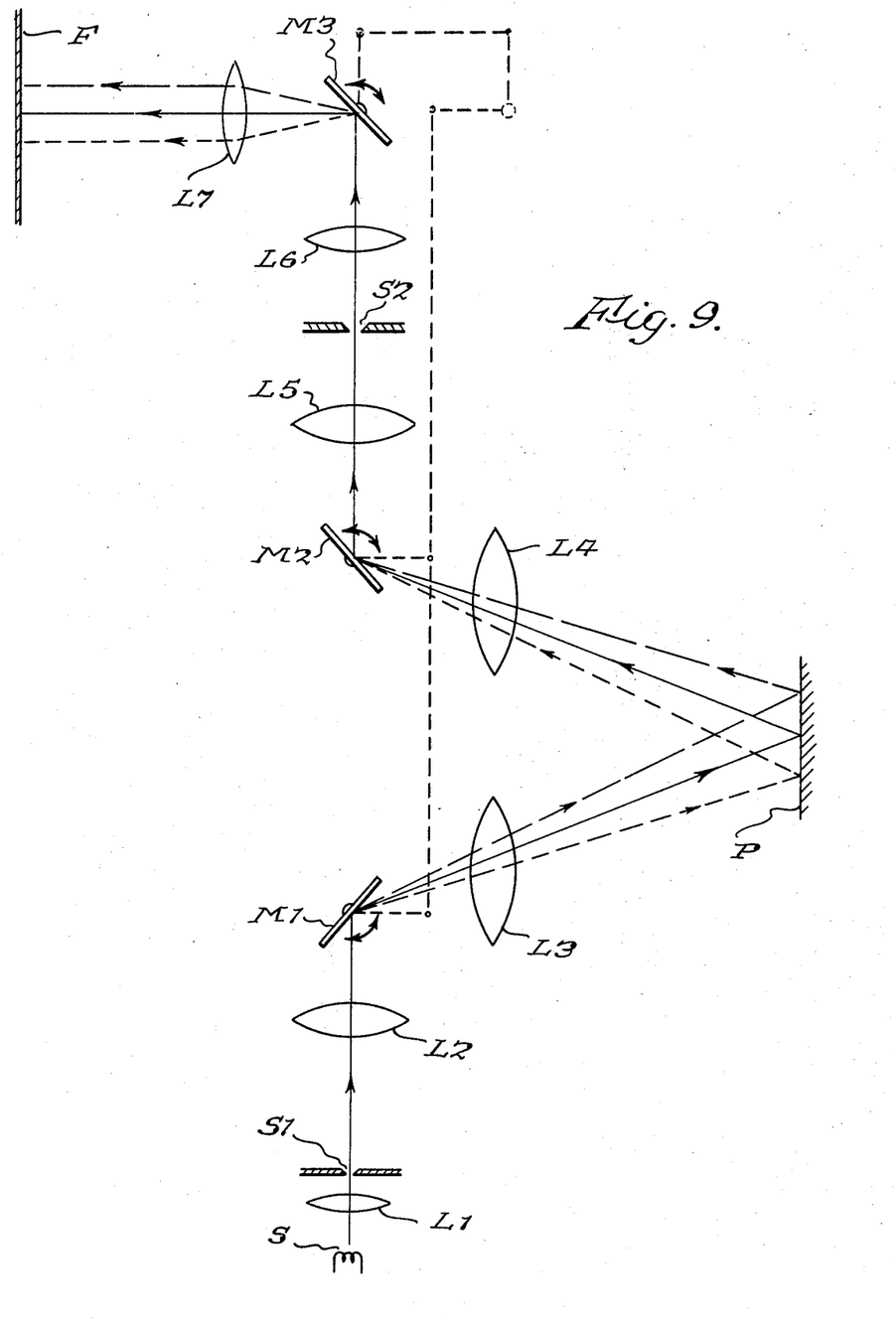
FIG. 9 is a plan diagram of a fourth exemplary embodiment of the invention, in which three synchronously rotating mirrors are used.

In FIG. 9 three synchronized rotating mirrors are used. This permits the use of separate objective lenses L3 and L4 for the illumination and image formation respectively, which will further improve the separation between illumination and viewing rays within the specimen. It will also eliminate another source of stray light in systems which utilize a single microscope objective, such as L3 in FIG. 1, namely interreflections between lens elements, which can result in some illumination light being reflected into the image forming path.

As in previous examples, light from the source is collected by condenser lens L1, passes through slit S1 and is collimated by lens L2. The light is then reflected by rotating mirror M1, and is focused by objective lens L3 at the object plane P. As mirror M1 rotates clockwise the image of slit S1 will scan across the plane P from right to left.

As was discussed in connection with FIG. 1, there will be in plane P a slit shaped area which is conjugate to slit S2. The position of slit S2 is adjusted so that its conjugate image at plane P is coincident with the image of slit S1. As mirror M2 rotates, the conjugates of slits S1 and S2 remain coincident as they scan across plane P.

Light passing through slit S2 is collimated by lens L6, reflected from rotating mirror M3 and brought to focus by lens L7 on image plane of film plane F. Mirror M3 rotates cynchronously with, but in the opposite direction to mirrors M1 and M2. The dashed line connecting mirrors M1, M2 and M3 illustrates how this synchronized rotation could be accomplished. Film F can be replaced by an eyepiece, for visual observation of the image.

A precaution necessary in the system of FIG. 9 is to tilt lenses L3 and L4 in order to have the illumination and viewing scans coincide within the specimen. The amount of the tilt can be found by employing the Scheimpflug condition. According to this principle, to image a given object plane onto a given image plane, one extends these planes until they intersect. The intersection will define a straight line. The plane of the objective lens must then be oriented so as to contain the same straight line. If the object is at optical infinity, as is the slit S1 in FIG. 9, then the plane of the lens must be parallel to the image plane. Thus in FIG. 9, the plane of lens L3 and of lens L4 is parallel to the specimen.

In general the magnification of each lens L3 and L4 will vary across the selected plane in the specimen. Therefore the size of the field must be limited to that area in which the illumination slit image and the viewing slit image overlap.

Figure 10:
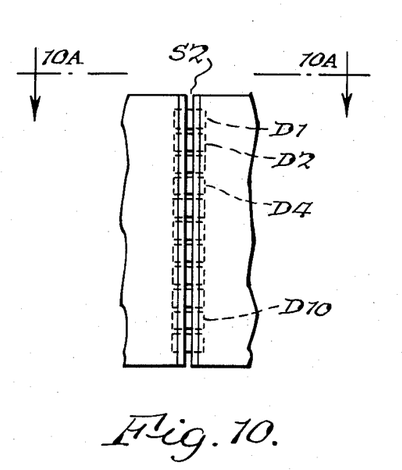
FIGS. 10, 10a and 10b illustrate an alternate method of image reconstruction which eliminates the need for a third reflection from the rotating mirror. An array of detectors is placed behind the second slit, and the output of the detectors is utilized to generate a television type display.
Figure 10A:
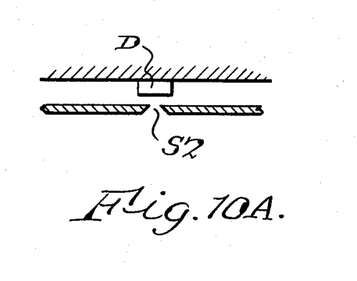
Figure 10B:
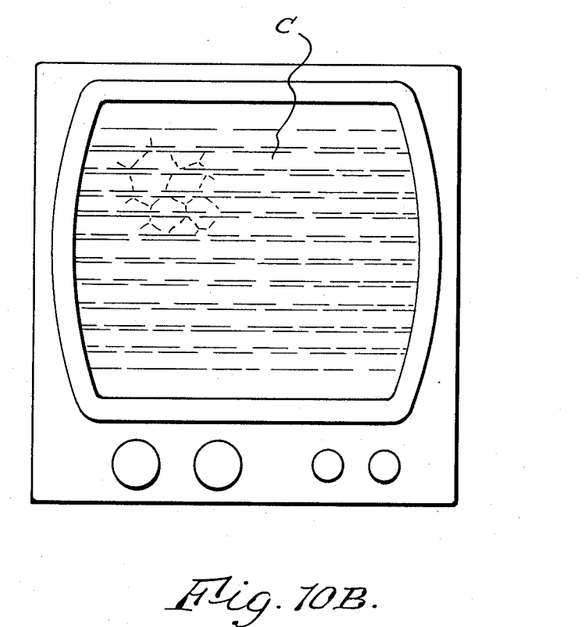

FIG. 10 illustrates another method for reconstructing the final image, utilizing a television type scan instead of the scanning mirror. In FIG. 10A, S2 is the slit S2 of FIGS. 1, 5, 7 or 9. Immediately behind the slit is a linear array of detectors, as shown at D1, D2, etc., in FIG. 10. The signal from each detector is displayed as a line or narrow band on the final display, illustrated in FIG. 10B. The display, C, could be a cathode ray tube.

It should be noted that in all previously described configurations the resolution achieved is not determined by the width of the slit S1 or S2. That is, in the plane of slit S2 there is an image of plane P, with two dimensional image detail. The slit S2 passes a rectangular shaped portion of this image. The image detail perpendicular to the long dimension of the slit as well as that parallel to the long dimension are preserved in the final reconstructed image. By contrast, in the system illustrated in FIG. 10, no image detail within the width of the slit S2 is preserved. That is, detector D1 essentially integrates all light striking it, and produces a signal proportional to the total light it receives, regardless of any image detail within the breadth of the slit or the length of the detector element. Therefore, the system illustrated in FIG. 10 will have a resolution which is limited by the width of the slit in the horizontal direction, and by the center-to-center spacing between detectors in the vertical direction.

In some applications, the signals from detectors D1, D2, etc., may be fed directly to a computer for analysis. This could be useful in cases in which the image is to be modified by any one of several image enhancing techniques, or the image detail is to be automatically counted and size distribution determined.

If the detectors D1, D2, etc. are sufficiently narrow, it will not be necessary to place a slit adjacent to the detectors. In this case the optical system will be arranged to image slit S1 directly onto the detector array.

Figure 11:
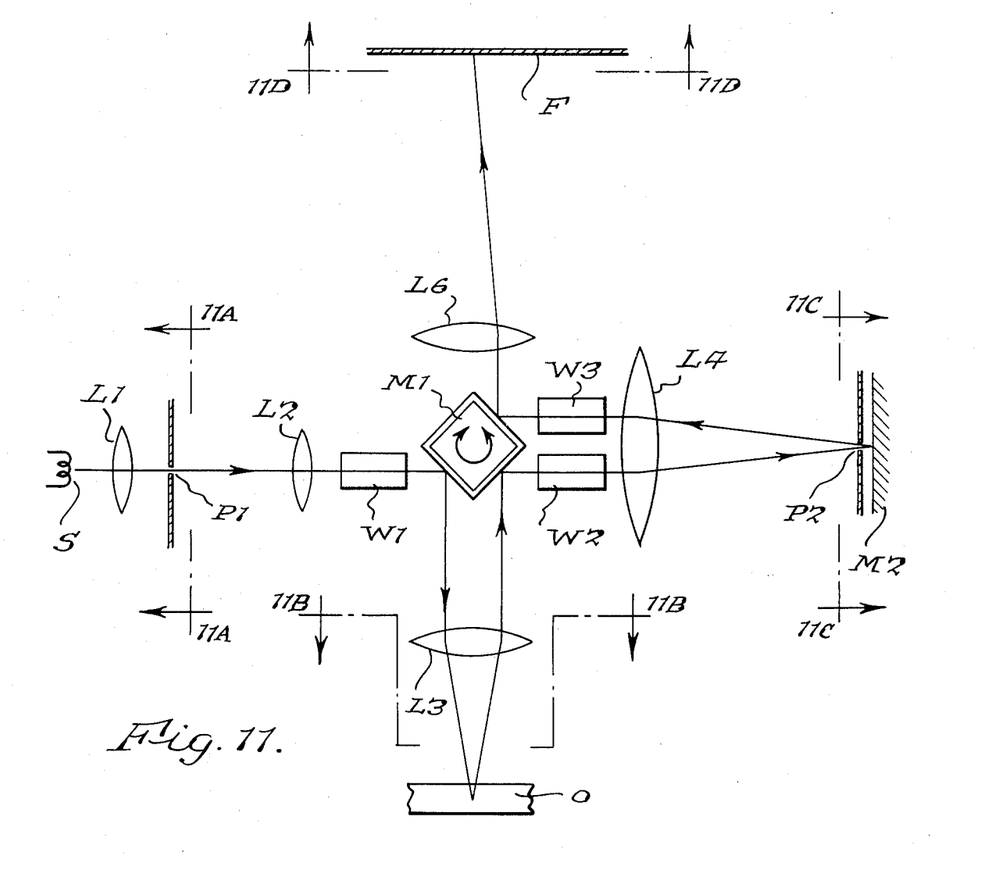
FIG. 11 illustrates a fifth exemplary embodiment of the invention, in which a pinhole source and pinhole aperture are used. In addition, three wavelength dispersing prisms are used, first to spread the light from the pinhole source into a slit shaped spectrum, next to recombine the wavelengths at the pinhole, and third, to spread the wavelengths into a slit shaped spectrum which is then scanned across the image plane.

FIGS. 2 and 3, as has been described, illustrate the advantage in using a narrow slit and in separating the illumination and viewing light rays within a volume of scattering medium. A further advantage is obtained if a pinhole is used instead of a slit. A nipkow disc accomplishes this type of scanning, but it requires great precision in fabrication. A relatively simple modification of the systems of FIGS. 1, 5, 7 or 9 can be used to accomplish this purpose. As shown in FIG. 11 a pinhole P1 is used in place of the slit S1, also a pinhole P2 in place of slit S2. A wavelength dispersing prism W1 is placed between the source pinhole P1 and the objective lens L3. It is oriented so that it produces a spectrum, R, fanning out in a direction perpendicular to the page. That is, the spectrum is in the form of a slit with the same position and orientation as the slit image in FIG. 1 extending lengthwise perpendicular to the page. This means that a given small area of the specimen 0 will be illuminated by a single wavelength, or more precisely a narrow band of wavelengths, say in the red portion of the spectrum. Another small area along the specimen will be illuminated by another narrow band of wavelengths, say in the green.

The light which returns from the specimen 0 passes through lens L3, reflects from mirror M1 as before, and then passes through dispersing prism W2. If prism W2 is oriented parallel to prism W1, light from the spectrum will be recombined to form a white light image of the pinhole P1 at pinhole P2. After reflection from mirror M2 the light will pass through lens L4 and be dispersed by prism W3 and be reflected again from rotating mirror M1. Thus a spectrum will be formed which will scan across the film plane F. The image will be reconstructed, in one dimension by the wavelength dispersion and in the other dimension by the scanning action.

If the image is recorded on black and white film, the spectrum will of course not be apparent. However, if recording in color is desired, it can be accomplished as follows. The pinholes P1 and P2 can be moved synchronously and slowly along the direction of the slit in FIGS. 1, 5, 7, 8 and 9. Then during one scan of the mirror a given point in the object 0 may be illuminated with orange light, and then yellow, and so on through the spectrum. Therefore the final image will be built up of many scans, each containing different color information, so that when all scans are complete each image point will have received light from the entire spectrum.

Figure 11A:
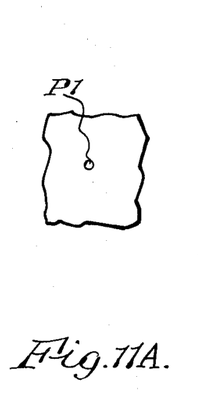
FIGS. 11A, 11B, 11C and 11D are schematic of views taken respectively in directions 11A, 11B, 11C and 11D in FIG. 11.
Figure 11B:
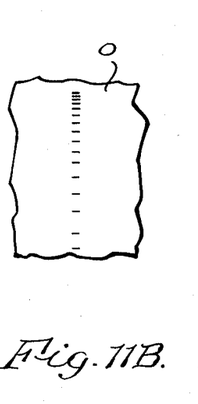
Figure 11C:
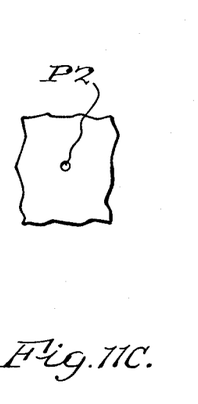

FIG. 11A illustrates the appearance of the pinhole aperture P1 in FIG. 11. FIG. 11B illustrates the appearance of the spectrum in the selected plane of the specimen, 0. Closely spaced lines indicate the blue end of the spectrum, widely spaced lines the red end of the spectrum. FIG. 11C illustrates the appearance of the pinhole aperture P2 in FIG. 11. The image of pinhole P1 as reconstructed by prism W2 and lens L4 is superimposed on this pinhole aperture P2. The dashed lines in FIG. 11D illustrate the instantaneous appearance of the spectrum which is formed in the film plane F of FIG. 11.

Figure 11D:
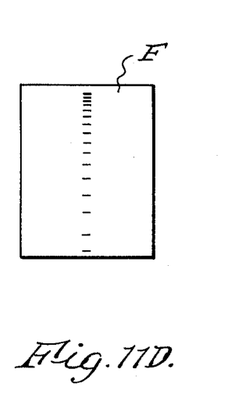

The rectangle in FIG. 11D represents the entire composite image, which is formed by the scanning of the spectrum in the horizontal direction.

FIG. 11 represents only one embodiment of this principle of two dimensional image slicing. One simplification is to use a single dispersing prism instead of prisms W1 and W2. The single prism is placed between the rotating mirror and the objective lens L3. The relay system in FIG. 4 provides two possible positions, the first between mirror M1 and lens 51, the other between lenses 52 and L3.

Examples of variations which would be possible under this invention are:

In fluorescence microscopy, the illumination light will generally be of a shorter wavelength than the fluorescence which is emitted by the object. The invention can be used for fluorescence microscopy by adding filters which are known to those skilled in the art; an excitation filter in the illumination beam and a barrier filter in the image forming beam.

For dark field microscopy, the illumination light will be incident on the object at an angle of incidence such that light specularly reflected from the object will not be received by the image forming optical system. This can be accomplished in a number of ways. The simplest can be described with reference to FIG. 4. The image of the mirror apex is moved from the center of lens L3 to one side of lens L3 so that the image forming rays occupy the central portion of lens L3 and the illumination rays pass through the extreme outer portion of lens L3.

For differential interference microscopy, a polarizer and a Wollaston type of prism of appropriate design can be placed in the optical path between the mirror M1 and objective lens L3, in FIGS. 1 and 4.

For certain types of light sources it would not be necessary to use the first slit, e.g., S1 in FIG. 1. For example a ribbon filament tungsten lamp has the form of a slit and so the filament could be placed at the position of slit S1 and the system would perform as desired. Or a laser may have a sufficiently narrow beam that a slit is not needed to restrict the size of the beam. In this case it may be necessary to spread the laser beam in the direction perpendicular to the plane of the diagram by means of a lens or combination of lenses in order to have a slit shaped illumination beam at the object. Certain light emitting diodes provide a slit shaped source of light and could be used at the position of slit S1.

In the several configurations given here by way of example, the common features and the essential points remain: (a) the separation of incident and reflected light within the volume of the specimen by using a narrow slit of light, and (b) laying down a composite image of incrementally illuminated and imaged, slit-shaped portions of the specimen, such incremental images being substantially freed of stray light by means of an image field aperture in the middle of the imaging system. The various geometries shown all include these features. They differ only in matters relating to practical considerations of space, accessibility and the like, considerations not essential to the inventive concepts.

I claim:

1. A scanning optical system for producing an image of an object including a light source, means for directing slit shaped illumination light from said source to said object including a rotatable first mirror surface, a second mirror surface which is rotatable synchronously with said first mirror surface and which reflects light emanating from the object, means to image said light from said object onto an array of detectors and electrical circuitry for processing the signals from said array of detectors.

2. A scanning optical system as defined in claim 1 in which said electrical circuitry includes a computer.

3. A scanning optical system as defined in claim 1 in which said electrical circuitry includes a display device.

4. A scanning optical system for producing an image of an object including:
means to generate a narrow strip of light,
illumination means to sweep scan said light strip across an object to scan-illuminate said object,
projection means to project an image of said object and to sweep scan the same across an image station,
said illumination means and said projection means scanning in synchronism,
a stationary aperture at said image station to transmit at any instant the image of a strip-illuminated increment of said object to the exclusion of the image of the surrounding area of said object, and
image receiving means operating in synchronism with said illumination means and said projection means to receive from said stationary aperture a composite image of successive increments of said object, said composite image thus corresponding to the scan-illuminated whole of said object.

5. A scanning optical system as defined in claim 4 in which said image receiving means is a moving image receptor disposed adjacent to said aperture.

6. A scanning optical system as set forth in claim 4 in which said image receiving means includes an image relay system to relay images from said aperture to an image plane, and to sweep scan said relayed images across said image plane to lay down thereon a composite of successive increments of said object.

7. A scanning optical system as set forth in claim 4 in which said image receiving means is an array of photodetectors.

8. A scanning optical system as set forth in claim 4 in which said image receiving means is an image sensor, said image sensor being adapted to convert a light image to an electrical signal.

9. A scanning optical system as set forth in claim 4 wherein said image receiving means includes an array of optical fibers disposed adjacent to said aperture to transmit images therefrom to form said composite image.

10. A scanning optical system as defined by claim 9 further comprising means for scanning said array of optical fibers across said image receiving means in synchronism with means for sweep scanning said light strip across said object.

11. A scanning optical system as defined by claim 9 wherein the exit end of said optical bundle is adapted to scan across an image plane in synchronism with said illumination scan.

12. A scanning optical system as defined by claim 9 wherein said array of optical fibers is a linear array.

13. A scanning optical system as defined by claim 9 wherein said linear array comprises a plurality of detectors.

14. A scanning optical system as defined by claim 9 wherein illumination rays emitted by said illumination means and image forming rays reflected off of said object are separated except at the plane of said object.

15. A method for microscopically examining a predetermined object field or plane to produce an image of said object field or plane comprising the steps of:

(a) directing slit shaped illumination from a light source to said field or plane by means including a first rotatable mirror surface;

(b) reflecting light emanating from said field or plane by means of a second rotating mirror surface synchronized with the rotation of said first mirror surface; and (c) imaging said light emanating from said object field or plane after the reflection of step (b) onto an array of detectors to produce electrical signals.

16. The method as defined by claim 15 further comprising transmitting said signals to means for processing said signals from said array of detectors.

17. The method as defined by claim 15 further comprising the step of transmitting said signals from said array of detectors to means for processing said signals.

18. The method as defined by claim 17 wherein said means are electronic means.

19. The method as defined by claim 18 wherein said electronic means for processing said signals comprises a computer.

20. The method as defined by claim 18 wherein said electronic means further comprises a display device connected to said array of detectors and said method comprises displaying said image corresponding to said field or plane on said display device.

21. The method as defined by claim 20 wherein said array of detectors is arranged behind a slit and said method comprises passing said reflected light through said slit prior to reaching said photodetector array.

22. The method as defined by claim 15 wherein said object field or plane comprises biological tissue.

23. The method as defined by claim 22 wherein said biological tissue comprises the endothelial cell layer on the inner surface of the cornea of the human eye.

24. A method for microscopically examining a predetermined object field or plane to produce an image of said object field or plane comprising the steps of:

(a) generating a narrow strip of light;

(b) sweep scanning said light strip across said field or plane to scan illuminate said field or plane;

(c) projecting said sweep scanning in synchronism with said sweep scanning of step (b) an image of said field or plane across an image station;

(d) transmitting the image of a strip-illuminated increment of said field or plane to the exclusion of the image of the surrounding the area of said object from said image station through a stationary aperture means; and (e) receiving a composite image of successive increments of said object field or plane corresponding to the scan illuminated whole of said field or plane on an image receiving means.

25. The method as defined by claim 24 comprising receiving said composite image by means of a moving image receptor disposed adjacent to said aperture.

26. The method as defined by claim 24 comprising receiving said composite image by using an image relay system for relaying said image from said aperture to an image plane; sweep scanning said relayed image across said image plane; and depositing a composite of successive increments of said image of said object field or plane on said image plane.

27. The method as defined by claim 24 comprising receiving said composite image on an array of photodetectors.

28. The method as defined by claim 24 comprising receiving said composite image on an image sensor adapted to convert a light image to an electrical signal.

29. The method as defined by claim 24 comprising receiving said strip-illuminated increment on receiving means comprising an array of optical fibers acting as said aperture means and transmitting said composite image through said fibers to a third rotating mirror to reform said composite image.

30. The method as defined by claim 29 further comprising reforming said composite image by scanning the output of said optical fibers across an image plane in synchronism with said illumination scan of step (b).

31. The method as defined by claim 24 wherein said object field or plane comprises biological tissue.

32. The method as defined by claim 31 wherein said biological tissue comprises the endothelial cell layer on the inner surface of the cornea of the human eye.

33. A method for producing an optical image of an object with a scanning optical system comprising the steps of:

(a) directing illumination from a light source to said object by reflecting said illumination from a first rotating mirror surface;

(b) reflecting light emanating from said object with a second rotating mirror surface, said first and second mirror surfaces rotating synchronously;

(c) focusing said light reflected from said second mirror surface at an aperture; and (d) directing said light from said aperture to a final image plane by reflecting said light from a third rotating mirror surface rotating synchronously with said first mirror surface to produce an optical image of said object on said final image plane.

34. The method as defined by claim 33 comprising oscillating each of said first, second and third mirror surfaces about an axis substantially parallel to said mirror surfaces.

35. The method as defined by claim 33 which comprises directing said illumination light onto said object through a lens means different from the lens means used to image said object on said aperture.

36. The method as defined by claim 33 further comprising separating said illumination from said light source directed onto said object and said light emanating from said object except at the plane of the object which is imaged at the aperture.

37. The method as defined by claim 33 wherein said aperture is a second aperture and said method further comprises passing said illumination from said light source through a first aperture prior to reflecting said illumination from said first mirror surface.

38. The method as defined by claim 33 which comprises dispersing said illumination by passing said illumination through a first prism oriented so as to disperse the wavelengths of said illumination into a spectrum oriented perpendicular to the scan direction of said first rotatable mirror surface, focusing said reflected light with a second dispersing prism oriented approximately parallel to said first dispersing prism, and passing said light reflected from said third mirror surface through a third dispersing prism oriented whereby the resulting spectrum is approximately perpendicular to the scan direction of said third mirror surface.

39. The method as defined by claim 33 wherein said object comprises biological tissue.

40. The method as defined by claim 39 wherein said biological tissue comprises the endothelial cell layer on the inner surface of cornea of the human eye.

* * * * *